(12) United States Patent
Wilmott et al.

(10) Patent No.: US 9,357,770 B2
(45) Date of Patent: Jun. 7, 2016

(54) SUBSTANTIALLY SURFACTANT-FREE, SUBMICRON DISPERSIONS OF HYDROPHOBIC AGENTS CONTAINING HIGH LEVELS OF WATER MISCIBLE SOLVENT

(71) Applicant: Leading Edge Innovations, LLC, Branchburg, NJ (US)

(72) Inventors: James Michael Wilmott, Clinton, NJ (US); Michael Alan Ross, Nazareth, PA (US)

(73) Assignee: Leading Edge Innovations, LLC, Branchburg, NJ (US)

( * ) Notice: Subject to any disclaimer, the term of this patent is extended or adjusted under 35 U.S.C. 154(b) by 0 days.

(21) Appl. No.: 14/211,562

(22) Filed: Mar. 14, 2014

(65) Prior Publication Data
US 2014/0271877 A1 Sep. 18, 2014

Related U.S. Application Data

(60) Provisional application No. 61/801,055, filed on Mar. 15, 2013.

(51) Int. Cl.
| | | |
|---|---|---|
| *A61Q 19/00* | (2006.01) | |
| *A61K 8/04* | (2006.01) | |
| *A01N 25/04* | (2006.01) | |
| *A01N 55/00* | (2006.01) | |
| *A61K 8/49* | (2006.01) | |
| *A61Q 9/02* | (2006.01) | |
| *A61Q 13/00* | (2006.01) | |
| *A01N 31/08* | (2006.01) | |
| *A61K 8/891* | (2006.01) | |
| *A61K 8/25* | (2006.01) | |
| *A61K 8/34* | (2006.01) | |
| *A61K 8/73* | (2006.01) | |
| *A61Q 17/00* | (2006.01) | |
| *A61K 8/81* | (2006.01) | |
| *A61Q 19/10* | (2006.01) | |
| *A61K 8/02* | (2006.01) | |

(52) U.S. Cl.
CPC .............. *A01N 25/04* (2013.01); *A01N 31/08* (2013.01); *A01N 55/00* (2013.01); *A61K 8/0212* (2013.01); *A61K 8/0241* (2013.01); *A61K 8/04* (2013.01); *A61K 8/042* (2013.01); *A61K 8/25* (2013.01); *A61K 8/345* (2013.01); *A61K 8/4946* (2013.01); *A61K 8/73* (2013.01); *A61K 8/8152* (2013.01); *A61K 8/891* (2013.01); *A61Q 9/02* (2013.01); *A61Q 13/00* (2013.01); *A61Q 17/005* (2013.01); *A61Q 19/00* (2013.01); *A61Q 19/10* (2013.01); *A61K 2800/244* (2013.01); *A61K 2800/28* (2013.01); *A61K 2800/33* (2013.01); *A61K 2800/413* (2013.01); *A61K 2800/48* (2013.01); *Y10S 977/773* (2013.01); *Y10S 977/906* (2013.01)

(58) Field of Classification Search
None
See application file for complete search history.

(56) References Cited

U.S. PATENT DOCUMENTS

| | | |
|---|---|---|
| 3,208,911 A | 9/1965 | Oppliger |
| 3,964,500 A | 6/1976 | Drakoff |
| 4,152,416 A | 5/1979 | Spitzer et al. |
| 4,341,799 A | 7/1982 | Good |
| 4,364,837 A | 12/1982 | Pader |
| 4,465,619 A | 8/1984 | Boskamp |
| 4,606,913 A * | 8/1986 | Aronson .................. A61K 8/06 424/59 |
| 4,788,006 A | 11/1988 | Bolich, Jr. et al. |
| 5,011,701 A | 4/1991 | Baer et al. |
| 5,021,248 A | 6/1991 | Stark et al. |
| 5,637,291 A | 6/1997 | Bara et al. |
| 5,716,638 A * | 2/1998 | Touitou ......................... 424/450 |
| 5,928,632 A | 7/1999 | Reusch |
| 5,928,832 A | 7/1999 | Smith et al. |
| 6,068,961 A | 5/2000 | Dutoff et al. |
| 6,268,102 B1 | 7/2001 | Hopper et al. |
| 6,485,756 B1 | 11/2002 | Aust et al. |
| 6,863,914 B1 * | 3/2005 | Auweter ................ A23K 1/002 424/490 |
| 7,250,455 B2 | 7/2007 | Cody et al. |
| 7,270,832 B2 | 9/2007 | Bryson et al. |
| 7,709,445 B2 | 5/2010 | Soula et al. |
| 8,034,381 B2 | 10/2011 | Moschwitzer |
| 8,597,678 B2 * | 12/2013 | Fountain ....................... 424/450 |

(Continued)

FOREIGN PATENT DOCUMENTS

WO WO-0234218 A2 5/2002

OTHER PUBLICATIONS

AC Williams, BW Barry. "Penetration Enhancers." Advanced Drug Delivery Reviews, vol. 64, 2012, pp. 128-137, available online Sep. 13, 2012.*

(Continued)

*Primary Examiner* — Isaac Shomer
(74) *Attorney, Agent, or Firm* — Moser Taboada

(57) ABSTRACT

A composition is provided to apply to the skin, hair, or external mucosa of a human or animal, and a method for using the composition. The composition includes for example a composition for application to skin, hair or external mucosa comprising: a) dispersed submicron particles of hydrophobic agent(s) having average particle size from 100 nm to 999 nm; b) an aqueous-solvent fluid; and c) rheological modifying agent(s); wherein the aqueous-solvent fluid is 10% to 95% wt. of one or more water miscible solvent(s), 4.99% to 89.99% wt. water, and 0.01% to 10% wt. of the rheological modifying agent(s); and wherein the hydrophobic agents comprise 0.01 to 70% wt. of the skin, hair or mucosal composition; and wherein the composition is substantially surfactant-free.

21 Claims, No Drawings

(56) References Cited

U.S. PATENT DOCUMENTS

| | | | |
|---|---|---|---|
| 2003/0215470 A1 | 11/2003 | Wilmott et al. | |
| 2003/0215471 A1* | 11/2003 | Wilmott et al. | 424/401 |
| 2004/0082654 A1* | 4/2004 | Pesce et al. | 514/547 |
| 2005/0065239 A1 | 3/2005 | Cody et al. | |
| 2007/0087022 A1 | 4/2007 | Desai et al. | |
| 2007/0116761 A1 | 5/2007 | Desai et al. | |
| 2007/0122465 A1 | 5/2007 | Desai et al. | |
| 2007/0122468 A1 | 5/2007 | Desai et al. | |
| 2007/0154539 A1* | 7/2007 | Fountain | 424/450 |
| 2007/0264295 A1 | 11/2007 | Kantner | |
| 2008/0093586 A1 | 4/2008 | Koch et al. | |
| 2008/0102128 A1 | 5/2008 | Constancis et al. | |
| 2008/0274195 A1* | 11/2008 | Nicolosi et al. | 424/489 |
| 2009/0004278 A1 | 1/2009 | Aimi et al. | |
| 2009/0155409 A1 | 6/2009 | Sexton et al. | |
| 2009/0196972 A1 | 8/2009 | Monsalvve-Gonzalez et al. | |
| 2009/0226498 A1* | 9/2009 | Flugge-Berendes et al. | 424/411 |
| 2009/0280148 A1 | 11/2009 | Aimi et al. | |
| 2010/0143424 A1 | 6/2010 | Kanazawa | |
| 2010/0203121 A1 | 8/2010 | Toledano et al. | |
| 2010/0264364 A1 | 10/2010 | Wagner et al. | |
| 2010/0285113 A1 | 11/2010 | Shoichet et al. | |
| 2011/0281827 A1 | 11/2011 | Tamarkin et al. | |
| 2012/0027865 A1 | 2/2012 | Sahoo et al. | |
| 2012/0093718 A1 | 4/2012 | Parchment et al. | |
| 2012/0244134 A1 | 9/2012 | Chen et al. | |
| 2012/0308627 A1 | 12/2012 | Gunes et al. | |
| 2013/0004640 A1 | 1/2013 | Zhang et al. | |
| 2013/0064954 A1 | 3/2013 | Ochomogo et al. | |
| 2013/0122071 A1 | 5/2013 | Cathala et al. | |

OTHER PUBLICATIONS

Dr. Spiller. "How Other Ranges Work." http://www.drspiller.com.au/yourskin/howotherrangeswork, accessed Dec. 10, 2015, 2 printed pages.*

ICI Americas Inc. "The HLB System a Time-Saving Guide to Emulsifier Selection." ICI Americas Inc., Revised Mar. 1980, pp. 1-22.*

Wilmott et al., "Surfactant-Free, Submicron Hydrophobic Dispersions and Food Enhancement Therewith", U.S. Appl. No. 13/835,642, filed Mar. 15, 2013, p. 1-34.

International Search Report and Written Opinion of International Application No. PCT/US2014/025734, dated Aug. 14, 2014, 10 pages.

International Preliminary Report on Patentability mailed Sep. 24, 2015 for Application No. PCT/US2014/027727, 12 pages.

PCT International Search Report and Written Opinion, Application No. PCT/US2014/027727, 17 Pages, Date of Mailing Dec. 29, 2014.

\* cited by examiner

SUBSTANTIALLY SURFACTANT-FREE, SUBMICRON DISPERSIONS OF HYDROPHOBIC AGENTS CONTAINING HIGH LEVELS OF WATER MISCIBLE SOLVENT

CROSS-REFERENCE TO RELATED APPLICATIONS

This application claims the benefit of U.S. Provisional Application No. 61/801,055, filed Mar. 15, 2013, the entire contents of which are incorporated by reference.

BACKGROUND OF THE DISCLOSURE

1. Field of the Disclosure

Embodiments of the present invention generally relate to substantially surfactant-free submicron hydrophobic agent dispersions with high levels of water miscible solvent.

2. Description of Related Art

The current practices for combining a hydrophobic material (such as liquid, semi-solid, or solid) with a hydrophilic liquid requires the addition of agents that change the native properties of both the hydrophobic material and the hydrophilic liquids so that they more closely resemble one another. As the properties of the two phases converge because of the additives, they have a greater propensity to be stable for a commercially viable period of time. An important class of additives that can be used in these hydrophobic phase/hydrophilic phase combinations is the surface-active agent, which is typically referred to as a "surfactant". These surfactants have both hydrophobic and hydrophilic properties.

When one or more of these agents are incorporated into the hydrophobic phase, the hydrophilic phase, or both the agents will align themselves at the hydrophobic phase-hydrophilic phase interface or at the interface between the composition and the surrounding air. The force that exists at the hydrophobic phase-hydrophilic phase ("Interfacial Tension") is reduced, allowing the two phases to more favorably coexist. Similarly, the force that exists at the air-composition interface ("Surface Tension") is also reduced. A special sub-category of "surfactants" is called an emulsifier. When carefully selected, such emulsifiers have a wide range of surface-active properties. These materials not only lower the interfacial tension at the hydrophobic phase-hydrophilic phase interface but, with the input of shearing energy, they enable the formation of stable droplets of one phase within the other. The resulting product is called an emulsion. In many cases such emulsions are prepared by heating the hydrophobic and hydrophilic phases to a temperature of 70° C. or greater before combining the two phases. The purpose of heating the phases is to ensure that all semi-solid and solid hydrophobic materials used are melted, and that the two phases have a low enough viscosity so the two phases can mix freely. The hydrophobic and hydrophilic phases are typically mixed together until they achieve a homogeneous appearance. Thereafter, they are cooled to ensure the formation of appropriately sized droplets, which is usually on average in the 3 micron to 10 micron range. Such emulsions typically have a homogeneous, opaque, white appearance due to their particle size.

These emulsions present difficulties in that the processing that creates stable emulsions is difficult to scale from the laboratory to production, and they are not amenable to maintaining emulsion stability upon dilution. Moreover, the stability of these emulsions is particularly problematic when the hydrophilic phase contains significant amounts of a water-miscible solvent.

SUMMARY

Provided are topically applied compositions containing high levels of a water miscible solvent and one or more substantially surfactant-free submicron dispersions of hydrophobic agents. In one embodiment, provided is a composition for application to skin, hair or external mucosa comprising one of: (A) the skin, hair or mucosal composition comprising (1): a) a substantially surfactant-free dispersion of submicron particles of hydrophobic agent(s) in an aqueous-solvent fluid, wherein the substantially surfactant-free dispersion of submicron particles of hydrophobic agent(s) has an average particle size from 100 nm to 999 nm, and wherein the hydrophobic agent(s) comprise about 0.01% wt. to about 70% wt. of the dispersion composition; and b) rheological modifying agent (s); wherein a resultant aqueous-solvent fluid, including the aqueous or aqueous-solvent fluid of the dispersion, is 10% to 95% wt. of one or more water miscible solvent(s), and 4.99% to 89.99% wt. water, and 0.01% to 10% wt. of the rheological modifying agent(s); or (B) the skin, hair or mucosal composition comprising (2): 1) dispersed submicron particles of hydrophobic agent(s) having average particle size from 100 nm to 999 nm; 2) an aqueous-solvent fluid; and 3) rheological modifying agent(s); wherein the aqueous-solvent fluid is 10% to 95% wt. of one or more water miscible solvent(s), 4.99% to 89.99% wt. water, and 0.01% to 10% wt. of the rheological modifying agent(s); and wherein the hydrophobic agents comprise 0.01 to 70% wt. of the skin, hair or mucosal composition; and wherein the composition is substantially surfactant-free. Additional solutes may be present in the aqueous-solvent fluid or resultant aqueous-solvent fluid.

In embodiments, 80% weight or more of the water miscible solvent is a mono-, di- or poly-hydroxy compound of formula A:

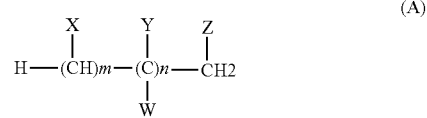

where X, Y and Z are independently —H or —OH; W is independently —H or —CH$_3$; m is 0 or 1; and n is an integer from 0 to 6.

Further provided is a method of applying a therapeutic agent to skin, hair or external mucosa comprising applying to such tissue any composition of the invention that comprises an effective amount of the therapeutic agent. A therapeutic agent can be a hydrophobic agent used in the dispersion.

Further provided is a method of imparting a desirable tactile, olfactory, or visual property to a skin, hair or mucosal surface comprising applying to such tissue any composition of the invention that comprises an effective amount of one or more aesthetic modifying agents. A given aesthetic modifying agent can be a hydrophobic agent used in the dispersion.

DETAILED DESCRIPTION

A number of compositions usefully employ as solvent a mixture of water and a water miscible solvent, such as ethanol or glycerin. For example, hand sanitizers, cooling colognes, cooling body lotions, shaving lubricants (e.g., shave gels), exfoliating compositions, and the like. It is desirable that these compositions contain hydrophobic agent(s), such as those that are aesthetic modifying agents in that they impart a desirable tactile, olfactory, or visual property to an animal (such as a human) skin, hair or mucosal surface to which the compositions are applied. Further, these compositions contain one or more hydrophobic agents, such as those that are therapeutic agents in that they treat disorders of human (or animal) skin, hair or mucosal tissue to which they are applied. However, it is because of the high water-miscible solvent content of the compositions, standard emulsification practices are no longer feasible, and, as a consequence, they are aesthetically unappealing to the user and the base selections for the hydrophobic therapeutic agents are very limited.

It has now been unexpectedly found that substantially surfactant-free submicron dispersions of hydrophobic agents in water or aqueous-solvent fluids can easily be scaled from the laboratory to production, and can be readily incorporated into a composition containing water and high levels of water miscible solvents which are stable for a commercially viable period of time. Further, these substantially surfactant-free dispersions of hydrophobic agents can greatly enhance the aesthetic and therapeutic properties of the composition. Further, these substantially surfactant-free dispersions of hydrophobic agents can be easily diluted in the composition post-production to deliver the desired level of therapeutic agents and the desired aesthetic properties. When the aqueous-solvent fluid is described herein, it will be recognized that the aqueous fluid or water miscible solvent can be sourced from a concentrated starting dispersion, or from materials used to dilute such a starting dispersion of submicron particles.

The compositions can contain hydrophilic aesthetic modifying agents and therapeutic agents which are believed to reside in the composition outside of the dispersion particles of hydrophobic agents.

A "hydrophobic agent" according to the invention has a solubility of less than about 0.1% by weight in water. Generally, the dielectric constant of the solvent provides a rough measure of a solvent's polarity. The strong polarity of water is indicated, at 20° C., by a dielectric constant of 80.10. Materials with a dielectric constant of less than 15 are generally considered to be nonpolar. In embodiments, the "hydrophobic agent" component(s) are substantially non-polar, in that 90% wt. or more are non-polar by this dielectric constant measure. In embodiments, 95% or 99% wt. or more of the hydrophobic agent component(s) are non-polar.

A "surfactant" is an amphiphilic compound with CMC greater than $10^{-8}$ mol/L.

A composition is "substantially surfactant-free" or "substantially free of surfactant" when the amount of surfactant(s) (CMC greater than $10^{-8}$ mol/L) are not an amount sufficient to materially lower the surface tension of an aqueous fluid. Moreover, in a "substantially surfactant-free" or "substantially free of surfactant" composition, amphiphilic compounds with a critical micelle concentration (CMC) of $10^{-8}$ mol/L or lower can be present for example in amounts of 1 part weight to 5 parts weight of other hydrophobic agents, or less.

In embodiments where the submicron dispersions of hydrophobic agent particles are substantially free of surfactants, the weight ratio of hydrophobic agent(s) to surfactant molecules(s) is 10 or more. In embodiments, the ratio is 100 or 200 or 500 or 1000 or more. Such minor amounts of surfactants can be composed of anionic, cationic or non-ionic surfactant molecules.

An "aqueous-solvent fluid" according to the invention contains 10 to 95% water miscible solvents, 4.99% to 89.99% wt. water, and optional additional solutes.

A "water miscible solvent" of the current invention is one that can mix in all proportions with water, forming a homogeneous solution.

An "aqueous fluid" according to the invention can be water or a combination of 50% or more water and from 0 to 50% solutes other than water miscible solvents.

A "cosmetic" material according to the invention is one that is generally recognized as safe for application to improve the appearance or odor of human or animal skin or mucosa. A "dermatologically appropriate material" is one that is generally recognized as safe for application to human or animal skin or mucosa. In embodiments, all the materials of a composition containing a submicron substantially surfactant-free dispersion of hydrophobic agents are dermatologically appropriate materials.

"Hydrophobic agent particles" are colloidal droplets of hydrophobic agent(s), wherein at some temperature in the range of 20 to 90° C. the droplets would be liquid.

A colloid is a substance microscopically dispersed throughout another substance. A colloidal system consists of two separate phases: a dispersed phase (or internal phase) and a continuous phase (or dispersion medium) in which the colloid is dispersed.

A "submicron hydrophobic dispersion" is defined as a submicron suspension of hydrophobic agent particles in an aqueous fluid or an aqueous-solvent fluid with an average particle size of from 100 nm to 999 nm. In embodiments of the invention, 85% or more, or 90% or more, of the hydrophobic agent particles by weight have a size within 300 nm of the average particle size. In embodiments of the invention, 85% or more, or 90% or more, of the hydrophobic agent particles by weight have a size within 250 nm of the average particle size. In embodiments of the invention, 85% or more, or 90% or more, of the hydrophobic agent particles have a size within 200 nm of the average particle size. In embodiments of the invention, 85% or more, or 90% or more, of the hydrophobic agent particles have a size within 150 nm of the average particle size. In embodiments of the invention, 85% or more, or 90% or more, of the hydrophobic agent particles have a size within 100 nm of the average particle size. The hydrophobic agent particles are not included in the water-solvent-solute weight percentages. The submicron dispersion of hydrophobic agent particles can be reduced by the processes described herein, or as concentrated therefrom, or diluted therefrom.

To treat indications with a therapeutic agent, an "effective amount" of a therapeutic agent will be recognized by clinicians but includes an amount effective to treat, reduce, alleviate, ameliorate, eliminate or prevent one or more symptoms of the condition sought to be treated, or alternately, the condition sought to be avoided, or to otherwise produce a clinically recognizable favorable change in the condition or its effects.

In reciting that a composition of the invention has a given percentage of water-miscible solvent, it will be recognized that during formulation that total amount of the water miscible solvent can be contributed from (i) a concentrated dispersion of substantially surfactant-free submicron particles of hydrophobic agent(s), (ii) a separate aqueous-solvent fluid that may be mixed with the concentrated dispersion, or (iii) both. Similarly, the water can come from either or both sources.

The substantially surfactant-free submicron dispersions of hydrophobic agent particles can include one or more amphiphilic compounds with a CMC of $10^{-8}$ mol/L or lower.

In certain embodiments, examples of these amphiphilic compounds include but are not limited to one or more phospholipids having a net neutral charge at pH 7.4, such as phosphatidylcholine or phosphatidylethanolamine. In certain embodiments, the amphiphilic compound(s) are one or more phospholipids having a net negative charge at pH 7.4, such as a phosphatidylinositide, phosphatidylglycerol, or phosphatidic acid.

The amount of phospholipid if present can be from 0.1 or 1% (wt) to 15%, as a percentage of the total phospholipid+ hydrophobic agent that is not phospholipid. Such phospholipid can contain either saturated or unsaturated fatty acyl chains. The phospholipids may be subjected to the process of hydrogenation to minimize the level of unsaturation thereby enhancing their resistance to oxidation. Exemplary sources of hydrogenated phosphatidylcholine (lecithin) include, for example, Basis LP20H lecithin from Ikeda Corp., Japan.

The dispersion composition includes a rheological modifying agent. The rheological modifying agent can be present in the composition or in the substantially surfactant-free dispersion of hydrophobic agents in an amount from 0.01 to 10% wt, or 0.1 to 5%, or 0.2 to 2%. Rheological modifying agents are added in particular to help immobilize the particles of hydrophobic agents for still longer term stability of the submicron dispersions.

The dispersion of the invention may be produced, in precursor form, by mixing an aqueous fluid and hydrophobic agents using processing conditions known in the art including, but not limited to, sonication (Sonic Man, Matrical Bioscience, Spokane, Wash.), high pressure/high shear (e.g., utilizing Microfluidizer, Microfluidics Company, Newton, Mass.), freeze drying (Biochima Biophys Acta 1061:297-303 (1991)), reverse phase evaporation (Microencapsulation 16:251-256 (1999)), and bubble method (J Pharm Sci 83(3): 276-280).

In sonication, for example, high intensity sound waves bombard the product for predetermined period of time. In direct sonication, the sonication probe is directly applied into the composition for processing. In indirect sonication, the composition is immersed into an ultrasonic bath, where it is exposed to the processing conditions for a predetermined period of time.

Precipitation utilizes compounds that are poorly-soluble in water, but soluble in organic solvents and surfactants that are water-soluble, to create emulsions. Two separate solutions are formed, one of an organic solvent and compounds, the other a mixture of surfactant dissolved in water. The two solutions are combined and an emulsion is created. The organic solvent is then evaporated out of the emulsion, causing the small spherical particles to precipitate, creating a suspension of submicron particles.

High pressure/high shear utilizes an aqueous phase and a hydrophobic phase. The aqueous phase is prepared into a solution with any other water-soluble Further, water miscible solvents are optionally added to create an aqueous-solvent phase. The hydrophobic phase is prepared into a mixture with any other non-water miscible or non-water soluble components. The two phases are subjected to pressure ranging from 10,000-50,000 psi. The resulting dispersion contains suspended submicron particles of hydrophobic agents.

In freeze drying, two available methods are thin film freezing and spray freeze drying. In spray freeze drying, for example, an aqueous solution containing active ingredients is atomized into the cold gas above a cryogenic liquid. The atomized particles adsorb onto the gas-liquid interface and aggregate there as submicron particles.

The production process is adapted to obtain hydrophobic particles of the appropriate size. The substantially surfactant-free hydrophobic agent particles of the invention, which are typically mechanically created, differ from the typical micelles whose creation is dependent on surfactant. The particles of the dispersion of the invention are believed to be stable primarily due to small size, rather than surfactant effects. This stability enhancement is defined by Stokes' Law which is illustrated in an equation relating the terminal settling or rising velocity of a smooth sphere in a viscous fluid of known density and viscosity to the diameter of the sphere when subjected to a known force field. This equation is $V=(2gr^2)(d1-d2)/9\mu$, where V=velocity of fall (cm/sec), g=acceleration of gravity (cm/sec$^2$), r=radius of particle (cm), d1=density of particle (g/cm$^3$), d2=density of medium (g/cm$^3$), and $\mu$=viscosity of the medium (dyne sec/cm$^2$). Using this equation, with all other factors being constant, a 200 nm hydrophobic agent particle has a velocity of fall that is 680 times slower than one of identical composition having a 5 micron particle size of a standard emulsion.

The substantially surfactant-free submicron dispersion can be created by mixing the hydrophobic agents with an aqueous fluid or an aqueous-solvent fluid. The precursor form is generally of higher concentration of hydrophobic agent, and can be, without limitation, diluted with a mixture of solvent, water, and a rheological modifying agent.

The composition may be produced with a shear that creates in combination with pressure an average particle size of between about 100 nm to about 999 nm, such as between about 100-500 nm, or 150-300 nm. The process can, for example, without limitation, include a rapid return to atmospheric pressure. Embodiments include wherein 85% or more, or 90% or more, of the particles by weight or, in other embodiments, by volume, are within one of the above-cited ranges.

Size distribution for a dispersion can be measured by a Nanotrac particle size analyzer (Microtrac, Montgomeryville, Pa.), or a Malvern ZetaSizer particle size analyzer (Malvern Instruments Ltd. Malvern, UK). Sizes recited herein are those determined by dynamic light scattering for spectrum analysis of Doppler shifts under Brownian Motion. Measurements are made using Mie scattering calculations for spherical particles. This reproducible methodology can be conducted with other available instruments for measuring average particle size and particle size distribution, including instruments from Horiba Scientific (Edison, N.J.).

The water miscible solvents are, in embodiments, 80% wt. or more of solvents according to formula A:

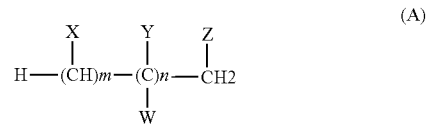

(A)

where X, Y and Z are independently —H or —OH; W is independently —H or —CH$_3$; m is 0 or 1; and n is an integer from 0 to 6. For example, the solvents can be mono, di, tri, tetra or penta alcohols, such as, but not limited to, methanol, ethanol, isopropyl alcohol, propanol, butanol, ethylene glycol, propylene glycol, butylene glycol, pentylene glycol, glycerol, tetritol, pentitol, 1,3 propane diol, and the like, or mixtures thereof. In embodiments, the solvents are, but are not limited to, 60% wt. or more ethanol, propanol, butylene glycol, glycerol, 1,3-propane diol, or mixtures thereof. In embodiments, the solvents are 60% wt. or more ethanol. In embodiments, the solvents are 70%, 80%, 90%, 95% or 99% wt. or more of such alcohols.

The water-miscible solvent of the aqueous-solvent fluid can have, without limitation, concentrations greater than 10%, or 20%, or 30% wt. in the aqueous-solvent fluid, or less than 95%, 90%, or 80%, or 70% wt, or a range therebetween. The water of the aqueous-solvent fluid can have, without limitation, concentration greater than 4.99%, or 10%, or 20%, or 30% wt. in the aqueous-solvent fluid, or less than 89.99%, or 80%, or 70% wt, or a range therebetween.

The hydrophobic agents can be present in the substantially surfactant-free submicron hydrophobic agent dispersion composition in an amount of 0.01% wt. to 90%, or 5% to 80%, or 10% to 60%, by weight.

The hydrophobic agents can include aesthetic modifying agents or therapeutic agents.

For example, 0.01% wt. to 90%, or 0.5% to 80%, or 1% to 60%, by wt. of the dispersion composition can be hydrophobic agents.

In embodiments, the skin, hair or mucosal composition can be for example 0.01% wt. to 70% wt, or 0.5% to 60%, or 1% to 50% hydrophobic agents.

Suitable therapeutic agents include, but are not limited to, anti-acne agents, antimicrobial agents, anti-inflammatory agents, analgesics, anti-erythemal agents, anti-pruritic agents, anti-edemal agents, anti-psoriatic agents, anti-fungal agents, skin protectants, sunscreen agents, vitamins, antioxidants, scavengers, anti-irritants, anti-bacterial agents, antiviral agents, antiaging agents, photoprotection agents, hair growth enhancers, hair growth inhibitors, hair removal agents, antidandruff agents, anti-seborrheic agents, exfoliating agents, wound healing agents, anti-ectoparasitic agents, sebum modulators, immunomodulators, hormones, botanicals, moisturizers, astringents, sensates, antibiotics, anesthetics, steroids, tissue healing substances, tissue regenerating substances, amino acids, peptides, minerals, ceramides, biohyaluronic acids, skin bleaching ingredients, and any combinations of the foregoing.

Suitable therapeutic agents that are anti-acne agents include, but are not limited to, salicylic acid, retinoic acid, alpha hydroxy acid, benzoyl peroxide, sodium sulfacetamide, clindamycin, hydrocortisone, tetrahydrozoline, and mixtures thereof.

Suitable therapeutic agents that are antimicrobial agents include, but are not limited to, Benzalkonium chloride, Benzethonium chloride, Chlorhexidine gluconate, Chloroxylenol, Clindamycin, Cloflucarban, erythromycin, Fluorosalan, Hexachlorophene, Hexylresorcinol, Iodine complex, Iodine tincture, Para-chloromercuriphenol, Phenylmercuric nitrate, Thimerosal, Vitromersol, Zyloxin, Triclocarban, Triclosan, Methyl-benzethonium chloride, Nonyl phenoxypoly (ethyleneoxy) ethanol-iodine, Para-chloro-meta-xylenol, Providone-iodine complex, Poloxamer-iodine complex, Undecoylium chloride-iodine complex, and any combinations of the foregoing.

Suitable therapeutic agents that are anti-inflammatory agents include, but are not limited to, Alidoxa, Allantoin, Aloe Vera, Aluminum acetate, Aluminum hydroxide, Bismuth subnitrate, Boric acid, Calamine, Casein, microporous cellulose, Cholecalciferol, Cocoa butter, Cod liver oil, Colloidal oatmeal, Cysteine hydrochloride, Dexpanthenol, Dimethicone, Glycerin, alpha-bisabolol, sea whip extract, glycyrrhetinic acid and its salts and derivatives, Kaolin, Lanolin, Live yeast cell derivative, Mineral oil, Peruvian balsam, Petrolatum, Protein hydrolysate, Racemethionine, Shark liver oil, Sodium bicarbonate, Sulfur, Talc, Tannic acid, Topical starch, Vitamin A, Vitamin E, White petrolatum, Zinc acetate, Zinc carbonate, Zinc oxide, Hydrocortisone, Betamethasone, Ibuprofen, Indomethacin, Acetylsalicylic acid, Tacrolimus, Fluocinolone acetonide, Sodium sulfacetamide, and any combinations of the foregoing.

Suitable therapeutic agents that are analgesics include, but are not limited to, diphenhydramine, tripelennamine, benzocaine, dibucaine, lidocaine, tetracaine, camphor, menthol, phenol, resorcinol, matacresol, juniper tar, methylsalicylate, turpentine oil, capsicum, methyl nicotinate, beta-glucan, and any combinations of the foregoing.

Suitable therapeutic agents that are anti-erythemal agents include, but are not limited to, tetrahydrozoline and hydrocortisone, and any combinations of the foregoing.

Suitable therapeutic agents that are antipruritic agents include, but are not limited to, diphenhydramine, pramoxine, antihistamines, and any combinations of the foregoing.

Suitable therapeutic agents that are anti-edema agents, include, but are not limited to, pregnenolone acetate, tannin glycosides, and any combinations of the foregoing.

Suitable therapeutic agents that are antipsoriatic agents include, but are not limited to, calcipotriene, coal tar, anthralin, vitamin A, hydrocortisone, retinoic acid, alpha hydroxy acid, dovonex, salicylic acid, sunscreen agents, indomethacin, urea; anthralin, and any combinations of the foregoing.

Suitable therapeutic agents that are antifungal agents include, but are not limited to, clioquinol, haloprogin, miconazole nitrate, clotrimazole, metronidazole, tolnaftate, undecylenic acid, iodoquinol, and any combinations of the foregoing.

Suitable therapeutic agents that are skin protectants include, but are not limited to, cocoa butter, dimethicone, petrolatum, white petrolatum, glycerin, shark liver oil, allantoin, and any combinations of the foregoing.

Suitable therapeutic agents that are sunscreen agents include, but are not limited to, ethylhexyl methoxycinnamate, avobenzone, benzophenones, octocrylene, ethylhexyl salicylate, homomethyl salicylate, triethanolamine salicylate, menthyl anthranilate, PABA, octyl dimethyl PABA, 2-ethoxyethyl p-methoxycinnamate, phenylbenzimidazole sulfonic acid, titanium dioxide, zinc oxide, and any combinations of the foregoing.

Suitable therapeutic agents that are antioxidants include, but are not limited to, scavengers for lipid free radicals and peroxyl radicals, quenching agents, astaxanthin, tocopherol, butylated hydroxytoluene (BHT), beta carotene, vitamin A, ascorbic acid and aliphatic derivatives, ubiquinol, ferulic acid, azelaic acid, thymol, catechin, sinapic acid, ethylenediaminetetraacetic acid (EDTA), lactoferrin, rosmariquinone, hydroxytyrosol, sesamol, 2-thioxanthine, nausin, malvin, carvacone, chalcones, glutathione isopropyl ester and other aliphatic derivatives, xanthine, melanin, guanisone, loporphyrins, 8-hydroxyxanthine, 2-thioxanthione, vitamin B12, plant alkaloids, catalase, quercetin, tyrosine, superoxide dismutase (SOD), cysteine, methionine, genistein, nordihydroguaiaretic acid (NDGA), procyanidin, hamamelitannin, ubiquinone, trolox, licorice extract, propyl gallate, and any combinations of the foregoing.

Suitable therapeutic agents that are vitamins include, but are not limited to, vitamin E, vitamin A palmitate, vitamin D, vitamin F, vitamin B6, vitamin B3, vitamin B12, vitamin C, ascorbyl palmitate, vitamin E acetate, biotin, niacin, dl-panthenol, and any combinations of the foregoing.

Note that the therapeutic agents can be hydrophobic, in which case they will associate with the hydrophobic agent particles, or hydrophilic, in which case they will associate with the aqueous-solvent fluid.

In embodiments, hydrophobic therapeutic agents comprise 60% wt. or less of the substantially surfactant-free submicron hydrophobic agent dispersion composition.

Examples of aesthetic modifying agents include without limitation C2-C26 alkyls substituted with 2-24 hydroxyls, where all of the hydroxyls of the foregoing compounds are independently acylated with a saturated, unsaturated, linear, branched or cyclic C1-C24 alkane. In embodiments, the substituted C2-C26 alkyls are reduced sugars (i.e., of the general formula $C_iH_{2i+2}O_n$).

An example of a hydrophobic aesthetic modifying agent is a compound having the formula $C_pH_{(2p+2-q)}$ where p is an integer greater than or equal to 6 and q is 0 or an even integer no greater than p. Such compounds include, but are not limited to, saturated and unsaturated, linear, branched, cyclic hydrocarbon chains. Examples of such compounds include without limitation mineral oil, petrolatum, permethyl fluids, polybutenes, polyisobutenes, and mixtures thereof.

Another example of a hydrophobic aesthetic modifying agent has formula B:

or formula C:

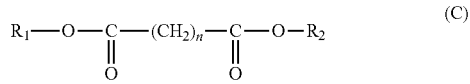

where $R_1$ is a saturated or unsaturated, linear, branched or cyclic C1-C23 alkane group; $R_2$ is hydrogen or a saturated or unsaturated, liner, branched or cyclic C1-C24 alkane group; and n is an integer from 0 to 20. Examples of such aesthetic modifying agents include, but are not limited to, isopropyl palmitate and diisopropyl adipate.

Still another aesthetic modifying agent is silicone. Silicone may provide lubrication and/or shine to the formulation. Preferably, the silicone is insoluble in water. Suitable water-insoluble silicone materials include, but are not limited to, polysiloxanes, cyclic siloxanes, polyalkylsiloxanes, polyarylsiloxanes, polyalkylarylsiloxanes, polysiloxane gums and polyethersiloxane copolymers. Examples of suitable silicone materials are disclosed in U.S. Pat. Nos. -36-4,788,006; 4,341,799; 4,152,416; 3,964,500; 3,208,911; 4,364,837 and 4,465,619, all of which are incorporated herein by reference for their teachings on silicone materials.

Another suitable hydrophobic material which can be suspended in the formulation has formula D:

wherein $M^+$ is $N^+R_3R_4R_5R_6$; wherein $R_3$, $R_4$, and $R_5$, are each independently hydrogen or a saturated or unsaturated, linear or branched alkane or hydroxyalkane group having from 1 to 10 carbon atoms; and $R_6$ is a saturated or unsaturated, linear, branched or cyclic alkyl or substituted alkane group having 2 to 24 carbon atoms. An example of such a material is dimethyl lauramine oleate.

The temperature of operation used to produce the substantially surfactant-free submicron dispersion of hydrophobic agents is generally between about 15° C. and about 30° C. In certain embodiments, the process avoids temperatures in excess of about 50° C., or in excess of about 60° C. However certain embodiments may require a temperature exceeding 60° C. to melt the hydrophobic agent.

The dispersion includes a rheological modifying agent. Such agents are known in the art and include, but are not limited to, those set forth in the following table adapted from www.foodadditives.org/food_gums/common.html

TABLE

| Rheological Agents |
|---|
| Agar-agar - a gum consisting of two repeating units of polysaccharides: alpha-D-galactopyranosyl and 3,6-anhydro-alpha-L-glactopyranosyl derived from red seaweed. Traditional agar-agar can bind approximately 100 times its weight in water when boiled, forming a strong gel that is often used as a stabilizer or thickener. A recent application of agar-agar is replacing gelatin as the gelling agent in dairy products, such as yogurt. Agar-agar is a non-animal gel source which is suitable for vegetarians and people with religious dietary restrictions (Kosher/Halal). |
| Alginate - is a polysaccharide, like starch and cellulose, and is derived from brown seaweed. Alginate provides properties in processed foods and beverages such as gelling, viscosifying, suspending and stabilizing. Alginate gelling may be achieved using calcium under controlled conditions. It employs the combination of alginate, a slowly soluble calcium salt and a suitable calcium sequestrant, such as a phosphate or citrate. The process may be performed at neutral or acid pH. |
| Carrageenan - a water soluble gum derived from red seaweeds, such as *Eucheuma*, *Gigartina*, and *Chondrus*. Carrageenan is a sulfated linear polysaccharide of D-galactose and it has a strong negative charge, thereby allowing it to stabilize gels or act as a thickener. Carrageenan is found in numerous products, ranging from toothpaste to soy milk. It is used to suspend cocca solids in beverages, for example, and can be used in meats to reduce cooking losses. |
| *Cassia* Gum - is a naturally occurring galactomannan found in the endosperm of *cassia tora* and *obtusifolia* seeds. It is an effective thickener and stabilizer for a broad range of food applications. *Cassia* gum has excellent retort stability and forms strong synergistic gels with other hydrocolloids including carrageenan and xanthan gum. Human food grade *cassia* gum is specially processed to meet rigorous purity standards. |
| Cellulose Gum - Carboxymethyl Cellulose (CMC), or cellulose gum is an abundant and natural polysaccharide found in all plants. Cellulose gum is a water-soluble gum that is based on cellulose. Cellulose gum has been used in food products for over 50 |

| TABLE-continued |
|---|
| Rheological Agents |
| years as a thickener and stabilizer. Typical uses are in instant beverages, where it provides texture, baked goods, where it prevents staling, and ice-cream, where it prevents the formation of ice-crystals that can be formed from frequent freezing and rethawing.<br>Gellan Gum - a food gum that is primarily used as a gelling or thickening agent. It can be used in fortified beverages to suspend protein, minerals, vitamins, fiber and pulp. Gellan gum also suspends milk solids in diluted milk drinks. Gellan gum can act as a fluid gel, having a wide range of textures, and can exist as a light pourable gel or a thick, spreadable paste. Gellan gum is a non-animal gel source which is suitable for vegetarians and people with religious dietary restrictions (Kosher/Halal).<br>Guar Gum - a carbohydrate consisting of mannose and galactose at a 2:1 ratio that can swell in cold water. Guar gum is one of the most highly efficient water-thickening agents available to the food industry and is widely used as a binder and volume enhancer. Its high percentage of soluble dietary fiber (80 to 85%), means that it is often added to bread to increase its soluble dietary fiber content. Guar gum is also commonly used to thicken and stabilize salad dressings and sauces and help improve moisture retention in finished baked goods.<br>Hydroxypropyl cellulose - cellulose is an abundant and natural polysaccharide found in all plants. Hydroxypropyl cellulose is based on cellulose and is used in many food products to provide good foam stability. Hydroxypropyl cellulose is commonly found in whipped toppings where it stabilizes the foam and provides a long lasting whipped topping with dairy-like eating quality.<br>Konjac Gum- a polysaccharide from a plant known as elephant yam, which is commonly found in Asia. This gum can be used as a vegan substitute for gelatin and other thickeners. Its texture makes it ideal for jellies because of its high viscosity.<br>Locust Bean Gum - also called Carob bean gum, locust bean gum is derived from the seeds of the carob bean. Locust bean gum is used for thickening, water-binding, and gel strengthening in a variety of foods. It has synergistic interactions with other gums, such as xanthan or carrageenan, and can be used in applications such as dairy, processed cream cheese, and dessert gels.<br>Methylcellulose and Hydroxypropyl Methylcellulose - cellulose is an abundant and natural polysaccharide found in all plants. Methylcellulose and hydroxypropyl methylcellulose are based on cellulose and are used in many food products to provide texture, certain mouth feels and other desirable qualities. These gums are commonly found in soy burgers where they add meat-like texture to the vegetable proteins, in fried appetizers like mozzarella cheese sticks and onion rings where they create firm texture by reducing the uptake of frying oils, and in whipped toppings where they stabilize the foam structure to give long lasting creams.<br>Microcrystalline cellulose (MCC) - is a polysaccharide derived from naturally occurring cellulose similar to that found in fruits and vegetables. MCC can be used as a bulking agent, source of fiber and moisture regulator in processed foods. MCC may also be co-processed with carboxymethyl cellulose (CMC) to impart shear-thinning and heat stable properties. Additional properties in food and beverages from MCC/CMC co-processed products include gelling, viscosifying, suspending and stabilizing.<br>Pectin - a polysaccharide derived from plant material, mainly citrus fruit peels, apple peels, or sugar beets. Pectin is widely used to impart gel formation, thickening, and physical stability to a wide range of foods. It is mostly used in fruit-based products, including jams, jellies, confectioneries, and fruit drinks, but is also used in dairy applications such as drinking and spoonable yogurt.<br>Xanthan Gum - a highly branched polysaccharide of D-glucose, D-mannose, and D-glucuronic acid produced via bacterial fermentation using nutrient sources.. Xanthan gum, which is considered natural, is an excellent emulsion stabilizer in salad dressings and sauces and also is used in bakery fillings to prevent water migration from the filling to the pastry (which has strong water-binding properties). Xanthan gum can often be used to improve the shelf life of a product. |

Suitable rheological modifying agents further include, but are not limited to, phosphorylated starch derivative, carbohydrate-based rheological modifying agents, polymeric and copolymeric rheological modifying agents, inorganic rheological modifying agents, protein rheological modifying agents, polypeptide rheological modifying agents, and any combinations of the foregoing.

Examples of a phosphorylated starch derivative include, but are not limited to, starches containing a phosphate group. Suitable phosphorylated starch derivatives include, but are not limited to, hydroxyalkyl starch phosphates, hydroxyalkyl distarch phosphates, and any combination of any of the foregoing. Non-limiting examples of hydroxyalkyl starch phosphates and hydroxyalkyl distarch phosphates include: hydroxyethyl starch phosphate, hydroxypropyl starch phosphate, hydroxypropyl distarch phosphate (including sodium hydroxypropyl starch phosphate), and any combinations of the foregoing.

Non-limiting examples of suitable carbohydrate based rheological modifying agents include algin and derivatives and salts thereof (such as algin, calcium alginate, propylene glycol alginate, and ammonium alginate); carrageenan (*Chondrus crispus*) and derivatives and salts thereof (such as calcium carrageenan and sodium carrageenan); agar; cellulose and derivatives thereof (such as carboxymethyl hydroxyethylcellulose, cellulose gum, hydroxyethylcellulose, hydroxypropylcellulose, hydroxypropyl methylcellulose, and ethylcellulose); chitosan and derivatives and salts thereof (such as hydroxypropyl chitosan, carboxymethyl chitosan, and chitin); gellan gum; guar (*Cyamopsis tetragonoloba*) and derivatives thereof (such as guar hydroxypropyltrimonium chloride and hydroxypropyl guar); hyaluronic acid and derivatives thereof (such as sodium hyaluronate); dextran and derivatives thereof; dextrin; locust bean (*Ceratonia siliqua*) gum; starches (such as starch polyacrylonitrile copolymer-potassium salt and starch polyacrylonitrile copolymer-sodium salt); pectin; sclerotium gum; tragacanth (*Astragalus gummifer*) gum; xanthan gum and derivatives thereof; and any combinations of the foregoing. P Non-limiting examples of suitable polymeric and copolymeric rheological modifying agents include acrylates, methacrylates, polyethylene and derivatives thereof, and any combination of any of the foregoing. Suitable acrylates and methacrylates include, but are not limited to, carbomer and derivatives and salts thereof, acrylates/C10-C30 alkyl acrylate crosspolymer, acrylates/ceteth-20 itaconate copolymer, acrylates/ceteth-methacrylate copolymers, acrylates/steareth-20 methacrylate copolymers, acrylates/steareth-20 itaconate copolymers, acrylates/steareth-50 acrylate copolymers, acrylates/VA crosspolymers, acrylates/vinyl isodecanoate crosspolymers, acrylic acid/acrylonitrogen copolymers, ammonium acrylates/acrylonitrogen copolymers, glyceryl polymethacrylate, polyacrylic acid, PVM/MA decadiene crosspolymer, sodium acrylate/vinyl isodecanoate crosspolymers, sodium carbomer, ethylene/acrylic acid copolymer, ethylene/VA copolymer, acrylates/acrylamide copolymer, acrylate copolymers, acrylates/hydroxyester acrylate copolymers, acrylate/octylarylamide copolymers, acrylates/PVP copolymers, AMP/acrylate copolymers, butylester of PVM-MA copolymer, carboxylate vinyl acetate terpolymers, diglycol/CHDM/isophthalates/SIP copolymer, ethyl ester of PVM-MA copolymer, isopropyl ester of PVM-MA copolymer, octylacrylamide/acrylate/butylaminoethyl methacrylate copolymers, polymethacrylamidopropyltrimonium chloride, propylene glycol oligosuccinate, polyvinylcaprolactam, PVP, PVP/dimethylaminoethylmethacrylate copolymer, PVP/DMAPA acrylate copolymers, PVP/carbamyl polyglycol ester, PVP/VA copolymer, PVP/VA vinyl propionate copolymer, PVP/vinylcaprolactam/DMAPA acrylate copolymers, sodium polyacrylate, VA/butyl maleate/isobornyl acrylate copolymers, VA/crotonates copolymer, VA/crotonates vinyl neodecanoate copolymer, VA/crotonates/vinyl propionate copolymer, vinyl caprolactam/PVP/dimethylaminoethylmethacrylate copolymer, hydroxyethyl Acrylate/Sodium Acryloyldimethy Taurate Copolymer, and any combinations of the foregoing.

Non-limiting examples of suitable inorganic rheological modifying agents include clays and derivatives thereof, silicates, silicas and derivatives thereof, and any combination of any of the foregoing. Suitable clays and derivatives thereof include, but are not limited to, bentonite and derivatives thereof, such as quaternium-18 bentonite; hectorite and derivatives thereof, such as quaterniums; montmorillonite; and any combinations of the foregoing. Suitable silicates include, but are not limited to, magnesium aluminum silicate, sodium magnesium silicate, lithium magnesium silicate, tromethamine magnesium aluminum silicate, and any combinations of the foregoing. Suitable silicas and derivatives thereof include, but are not limited to, hydrated silica, hydrophobic silica, spherical silica, and any combinations of the foregoing.

Suitable protein and polypeptide rheological modifying agents include, but are not limited to, proteins and derivatives and salts thereof, polypeptides and derivatives and salts thereof, and any combination of any of the foregoing. Non-limiting examples of protein and polypeptide rheological modifying agents include albumin, gelatin, keratin and derivatives thereof, fish protein and derivatives thereof, milk protein and derivatives thereof, wheat protein and derivatives thereof, soy protein and derivatives thereof, elastin and derivatives thereof, silk protein and derivatives thereof, and any combinations of the foregoing.

Particularly suitable rheological modifying agents include, but are not limited to, carbomer, acrylate/alkyl acrylate crosspolymers, acrylate/vinyl isododecanoate crosspolymer, xanthan gum, hydroxyethyl cellulose, locust bean gum, guar gum, and any combination of any of the foregoing. A suitable combination of rheological modifying agents comprises carbomer and an acrylate/alkyl acrylate copolymer, such as an acrylates/C10-C30 alkyl acrylate crosspolymer. According to the International Cosmetic Ingredient Dictionary and Handbook (7th ed., The Cosmetic, Toiletry, and Fragrance Association), carbomer is a homopolymer of acrylic acid crosslinked with an allyl ether of pentaerythritol, an allyl ether of sucrose, or an allyl ether of propylene. The term "acrylate/alkyl acrylate crosspolymer" includes, but is not limited to, copolymers of alkyl acrylates with one or more monomers of acrylic acid, methacrylic acid, or one of their short chain (i.e. C1-4 alcohol) esters, wherein the crosslinking agent is, for example, an allyl ether of sucrose or pentaerytritol. Preferably, the alkyl acrylates are C10-C30 alkyl acrylates. Examples of such copolymers include, but are not limited to, those commercially available as Ultrez-21, Ultrez-20, Carbopol™ 1342, Carbopol™ 1382, Pemulen™ TR-1, and Pemulen™ TR-2, from Novion, Cleveland, Ohio.

Particularly suitable rheological modifying agents include, but are not limited to, hydrophilic gelling agents, such as carboxyvinyl polymers (carbomer), acrylic copolymers (e.g., acrylate/alkyl acrylate copolymers), polyacrylamides, Hydroxyethyl Acrylate/Sodium Acryloyldimethyl Taurate Copolymers, polysaccharides (e.g. hydroxypropylcellulose), natural gums (e.g., xanthan gum), clays, and any combinations of the foregoing.

Examples of hydrophobic agents include but are not limited to, mono, di, tri, or poly alkyl (or alkenyl) esters or ethers of a di-, tri-, or polyhydroxy compound, such as glycerin, sorbitol or other polyol compound. Examples of such esters or ethers include but are not limited to, saturated and unsaturated, linear and branched vegetable oils, such a soybean oil, almond oil, castor oil, canola oil, cottonseed oil, grapeseed oil, rice bran oil, palm oil, coconut oil, palm kernel oil, olive oil, linseed oil, sunflower oil, safflower oil, peanut oil and corn oil. Useful saturated and unsaturated oils include those having 90% or more (molar) fatty acyl components with 6 to 30 carbon atoms, such as 6 to 24 carbons, or 12 to 24 carbons.

Examples of fatty acids providing fatty acyl components, or which provide hydrophobic agents include, without limitation, for example (from www.scientificpsychic.com/fitness/fattyacids.html):

TABLE

Common Fatty Acids

| Common Name | Carbon Atoms | Double Bonds | Scientific Name | Sources |
|---|---|---|---|---|
| Butyric acid | 4 | 0 | butanoic acid | butterfat |
| Caproic Acid | 6 | 0 | hexanoic acid | butterfat |
| Caprylic Acid | 8 | 0 | octanoic acid | coconut oil |
| Capric Acid | 10 | 0 | decanoic acid | coconut oil |
| Lauric Acid | 12 | 0 | dodecanoic acid | coconut oil |
| Myristic Acid | 14 | 0 | tetradecanoic acid | palm kernel oil |
| Palmitic Acid | 16 | 0 | hexadecanoic acid | palm oil |
| Palmitoleic Acid | 16 | 1 | 9-hexadecenoic acid | animal fats |
| Stearic Acid | 18 | 0 | octadecanoic acid | animal fats |
| Oleic Acid | 18 | 1 | 9-octadecenoic acid | olive oil |
| Ricinoleic acid | 18 | 1 | 12-hydroxy-9-octadecenoic acid | castor oil |
| Vaccenic Acid | 18 | 1 | 11-octadecenoic acid | butterfat |
| Linoleic Acid | 18 | 2 | 9,12-octadecadienoic acid | grape seed oil |
| Alpha-Linolenic Acid (ALA) | 18 | 3 | 9,12,15-octadecatrienoic acid | flaxseed (linseed) oil |
| Gamma-Linolenic Acid (GLA) | 18 | 3 | 6,9,12-octadecatrienoic acid | borage oil |
| Arachidic Acid | 20 | 0 | eicosanoic acid | peanut oil, fish oil |
| Gadoleic Acid | 20 | 1 | 9-eicosenoic acid | fish oil |
| Arachidonic Acid (AA) | 20 | 4 | 5,8,11,14-eicosatetraenoic acid | liver fats |
| EPA | 20 | 5 | 5,8,11,14,17-eicosapentaenoic acid | fish oil |
| Behenic acid | 22 | 0 | docosanoic acid | rapeseed oil |
| Erucic acid | 22 | 1 | 13-docosenoic acid | rapeseed oil |
| DHA | 22 | 6 | 4,7,10,13,16,19-docosahexaenoic acid | fish oil |
| Lignoceric acid | 24 | 0 | tetracosanoic acid | small amounts in most fats |

Fatty acyl compositions of some oils useful in the invention, reciting the rounded wt. percentage of some leading natural fatty acids, include without limitation the following (from www.scientificpsychic.com/fitness/fattyacids1.html):

TABLE

Fatty Acid Compositions of Hydrophobic Agents

| Oil or Fat | Unsat./Sat. ratio | Saturated | | | | | Mono unsatur. | Poly unsaturated | |
|---|---|---|---|---|---|---|---|---|---|
| | | Capr. Acid C10:0 | Laur. Acid C12:0 | Mryis. Acid C14:0 | Palm. Acid C16:0 | Stear. Acid C18:0 | Oleic Acid C18:1 | Linoleic Acid (ω6) C18:2 | Alpha Linolenic Acid (ω3) C18:3 |
| Almond Oil | 9.7 | — | — | — | 7 | 2 | 69 | 17 | — |
| Beef Tallow | 0.9 | — | — | 3 | 24 | 19 | 43 | 3 | 1 |
| Butterfat (cow) | 0.5 | 3 | 3 | 11 | 27 | 12 | 29 | 2 | 1 |
| Butterfat (goat) | 0.5 | 7 | 3 | 9 | 25 | 12 | 27 | 3 | 1 |
| Butterfat (human) | 1.0 | 2 | 5 | 8 | 25 | 8 | 35 | 9 | 1 |
| Canola Oil | 15.7 | — | — | — | 4 | 2 | 62 | 22 | 10 |
| Cocoa Butter | 0.6 | — | — | — | 25 | 38 | 32 | 3 | — |
| Cod Liver Oil | 2.9 | — | — | 8 | 17 | — | 22 | 5 | — |
| Coconut Oil | 0.1 | 6 | 47 | 18 | 9 | 3 | 6 | 2 | — |
| Corn Oil (Maize Oil) | 6.7 | — | — | — | 11 | 2 | 28 | 58 | 1 |
| Cottonseed Oil | 2.8 | — | — | 1 | 22 | 3 | 19 | 54 | 1 |
| Flaxseed Oil | 9.0 | — | — | — | 3 | 7 | 21 | 16 | 53 |
| Grape seed Oil | 7.3 | — | — | — | 8 | 4 | 15 | 73 | — |
| Illipe | 0.6 | — | — | — | 17 | 45 | 35 | 1 | — |
| Lard (Pork fat) | 1.2 | — | — | 2 | 26 | 14 | 44 | 10 | — |
| Olive Oil | 4.6 | — | — | — | 13 | 3 | 71 | 10 | 1 |
| Palm Oil | 1.0 | — | — | 1 | 45 | 4 | 40 | 10 | — |
| Palm Olein | 1.3 | — | — | 1 | 37 | 4 | 46 | 11 | — |
| Palm Kernel Oil | 0.2 | 4 | 48 | 16 | 8 | 3 | 15 | 2 | — |
| Peanut Oil | 4.0 | — | — | — | 11 | 2 | 48 | 32 | — |
| Safflower Oil* | 10.1 | — | — | — | 7 | 2 | 13 | 78 | — |

TABLE-continued

Fatty Acid Compositions of Hydrophobic Agents

| Oil or Fat | Unsat./ Sat. ratio | Saturated | | | | | Mono unsatur. | Poly unsaturated | |
| --- | --- | --- | --- | --- | --- | --- | --- | --- | --- |
| | | Capr. Acid C10:0 | Laur. Acid C12:0 | Mryis. Acid C14:0 | Palm. Acid C16:0 | Stear. Acid C18:0 | Oleic Acid C18:1 | Linoleic Acid (ω6) C18:2 | Alpha Linolenic Acid (ω3) C18:3 |
| Sesame Oil | 6.6 | — | — | — | 9 | 4 | 41 | 45 | — |
| Shea nut | 1.1 | — | 1 | — | 4 | 39 | 44 | 5 | — |
| Soybean Oil | 5.7 | — | — | — | 11 | 4 | 24 | 54 | 7 |
| Sunflower Oil* | 7.3 | — | — | — | 7 | 5 | 19 | 68 | 1 |
| Walnut Oil | 5.3 | — | — | — | 11 | 5 | 28 | 51 | 5 |

*Not high-oleic variety

The hydrophobic agents can be colorants, such as for example annatto oil, paprika oil, chlorphyll, lycopene, carotenoids. xanthophylls or the like. The hydrophobic agents can be essential nutrients, such as for example, vitamins such as Vitamin D and its derivatives, Vitamin A and its derivatives, Vitamin E and its derivatives, Vitamin K, Vitamin F, Vitamin P, and the like. Other such nutrients include for example lipoic acid, lycopene, phospholipids, ceramides, ubiqinone, sterols, flavonoids, cholesterol, sphingolipids, prostaglandins, docosahexaenoic acid, and the like.

The hydrophobic agents can be fragrances, such as for example terpenes, isoterpenenes, alkyl lactones, essential oils, natural oils such as vanilla, and the like. The hydrophobic agents can be aroma providers that impart aroma to or modify aroma of a topical composition.

The hydrophobic agents (including aesthetic modifying agents if present) can be present in the substantially surfactant-free dispersion composition in an amount of 0.01% wt. to 90%, or 5% to 80%, or 10% to 60%, by wt.

The submicron hydrophobic agent dispersion composition can contain other suitable adjuvants which may include, but are not limited to, pH adjusters, emollients, conditioning agents, chelating agents, colorants, fragrances, odor masking agents, non-dispersed actives, UV stabilizers, preservatives, and any combination of any of the foregoing. Suitable pH adjusters include, but are not limited to, aminomethyl propanol, aminomethylpropane diol, triethanolamine, citric acid, sodium hydroxide, acetic acid, potassium hydroxide, lactic acid, and any combination of any of the foregoing. Suitable conditioning agents include, but are not limited to, cyclomethicone, petrolatum, dimethicone, dimethiconol, silicone, quaternary amines, and any combination of any of the foregoing. The formulation can for example contain less than about 4.0% by weight of preservatives, based upon weight of total formulation, or from about 0.25% to about 3% by weight of preservatives, based upon weight of total formulation.

It is the small size of the dispersion particles that imparts stability. The small size minimizes the tendency of hydrophobic particles to coalesce. The commercially viable stability described above (180 days or more) allows a useful amount of time in which to store topical compositions to maintain product integrity.

The stability is further manifested in that two or more distinct dispersions can be mixed without decreasing the stability of the various component hydrophobic agent particles, or a dispersion can be diluted into aqueous fluid or aqueous-solvent fluid without decreasing the stability of the component hydrophobic agent particles.

Further, if hydrophobic agent A were not compatible with hydrophobic agent B when mixed, nonetheless a dispersion of the invention of hydrophobic agent A can be mixed with a dispersion of hydrophobic B, since the individual particles maintain their integrity. Silicone Oil and Olive Oil exemplify such incompatible hydrophobic agents.

In the methods of the invention, animals treated can include, without limitation, humans, domesticated animals (such as dogs, cats, hamsters, gerbils, guinea pigs, cattle, pigs, sheep, goats, horses, zebus, donkeys, mules, buffalos, camels, yaks, mice, rats, other rodents, gayals, rabbits, alpacas, vicunas, llamas, poultry, other domesticated birds, and the like), wild animals, and the like.

Hand Sanitizer

In certain embodiments of the invention formulated as hand sanitizers, the composition can include for example:

| | Embodiment A (by wt. %) | Embodiment B (by wt. %) |
| --- | --- | --- |
| Ethanol or isopropyl alcohol | 50-89.99 | 50-89.99% wt |
| Water miscible solvent(s) of Formula A that that are not ethanol or isopropyl alcohol | [1-25] | [2-15] |
| Substantially surfactant-free Submicron Hydrophobic dispersions that are skin conditioning modifying agents | [1-20] | [5-15] |
| Antioxidant | [0-0.2] | [0.02-0.1] |
| Thickener (rheological agent) | [0-3] | [0.1-1.75] |
| Substantially surfactant-free Submicron Hydrophobic dispersions that are aesthetic modifying agents | [1-20] | [5-15] |
| Water | [5-40] | [10-30] |
| Neutralizing agent | [0-7.5] | [0.2-5] |

Cologne

In certain embodiments of the invention formulated as colognes, the composition can include for example:

| | Embodiment A (by wt. %) | Embodiment B (by wt. %) |
| --- | --- | --- |
| Substantially surfactant-free Submicron Hydrophobic dispersions that are Fragrances | [0.01-20] | [0.2-10] |

-continued

|  | Embodiment A (by wt. %) | Embodiment B (by wt. %) |
|---|---|---|
| Ethanol | 50-89.99 | 50-89.99% wt |
| Water miscible solvent(s) of Formula A that is not ethanol | [1-35] | [2-20] |
| Silica, e.g. Spherical silica, or other inorganic mattifying agent | [0-10] | [0.5-15] |
| Antioxidant | [0-0.2] | [0.02-0.1] |
| Thickener (e.g., organic rheological agent) | [0-5] | [0.2-2.5] |
| Anti-irritant | [0-2] | [0.1-0.5] |
| Substantially surfactant-free Submicron hydrophobic dispersions that are aesthetic modifying agents | [0-30] | [2-20] |
| Water | [5-40] | [10-30] |
| Neutralizing agent | [0-7.5] | [0.2-5] |

Shave Gel or Cream

In certain embodiments of the invention formulated as shave gels or creams, the composition can include for example:

|  | Embodiment A (by wt. %) | Embodiment B (by wt. %) |
|---|---|---|
| Water miscible solvent(s) of Formula A | [10-60] | [20-50] |
| Urea, or other moisturizing agent | [0-10] | [1-5] |
| Antioxidant | [0-0.2] | [0.02-0.1] |
| Thickener (rheological agent) | [0-5] | [0.2-2] |
| Soothing Agent | [0-5] | [0.2-0.8] |
| Substantially surfactant-free Submicron hydrophobic dispersions that are aesthetic modifying agents or skin conditioning agents | [2-50] | [10-30] |
| Water | [20-90] | [30-70] |
| Neutralizing agent | [0-7.5] | [0.2-5] |

Exfoliator—Ethyl Alcohol Free

In certain embodiments of the invention formulated as ethyl alcohol-free exfoliators, the composition can include for example:

|  | Embodiment A (by wt. %) | Embodiment B (by wt. %) |
|---|---|---|
| Solvent(s) of Formula A that does not include ethanol | [5-50] | [7-25] |
| Exfoliating acids | [1-30] | [5-20] |
| Thickener (rheological agent) | [0-7.5] | [0.2-5] |
| Soothing Agent | [0-2] | [0.1-1] |
| Substantially surfactant-free Submicron hydrophobic dispersions that are aesthetic modifying agents or skin conditioning agents | [2-30] | [8-20] |
| Water | [20-90] | [30-70] |
| Neutralizing agent | [0-7.5] | [0.2-5] |

Exfoliating acids include but are not limited to, for example, lactic acid, salicylic acid, tartaric acid, glycolic acid, lactobionic acid, malic acid.

Exfoliator—with Alcohol

In certain embodiments of the invention formulated as alcohol exfoliators, the composition can include for example:

|  | Embodiment A (by wt. %) | Embodiment B (by wt. %) |
|---|---|---|
| Ethanol | [5-25] | [7-15] |
| Water miscible solvent of Formula A that is not ethanol | [5-40] | [7-25] |
| Exfoliating acids | [1-30] | [5-20] |
| Thickener (rheological agent) | [0-7.5] | [0.2-5] |
| Soothing Agent | [0-0.8] | [0.1-0.5] |
| Substantially surfactant-free Submicron hydrophobic dispersions that are aesthetic modifying agents or skin conditioning agents | [2-20] | [8-15] |
| Water | [20-90] | [30-70] |
| Neutralizing agent | [0-7.5] | [0.2-5] |

Body Lotion

In certain embodiments of the invention formulated as body lotions, the composition can include for example:

|  | Embodiment A (by wt. %) | Embodiment B (by wt. %) |
|---|---|---|
| Ethanol | [5-25] | [7-15] |
| Water miscible solvent of Formula A that is not ethanol | [5-40] | [7-25] |
| Thickener (rheological agent) | [0-7.5] | [0.2-5] |
| Soothing Agent | [0-0.8] | [0.1-0.5] |
| Substantially surfactant-free Submicron hydrophobic dispersions that are aesthetic modifying agents or skin conditioning agents | [2-20] | [8-15] |
| Water | [20-90] | [30-70] |
| Neutralizing agent | [0-7.5] | [0.2-5] |

All ranges recited herein include ranges therebetween, and can be inclusive or exclusive of the endpoints. Optional included ranges are from integer values therebetween (or inclusive of one original endpoint), at the order of magnitude recited or the next smaller order of magnitude. For example, if the lower range value is 0.2, optional included endpoints can be 0.3, 0.4, . . . 1.1, 1.2, and the like, as well as 1, 2, 3 and the like; if the higher range is 8, optional included endpoints can be 7, 6, and the like, as well as 7.9, 7.8, and the like. One-sided boundaries, such as 3 or more, similarly include consistent boundaries (or ranges) starting at integer values at the recited order of magnitude or one lower. For example, 3 or more includes 4 or more, or 3.1 or more.

The following embodiments are intended to demonstrate the versatility of substantially surfactant-free submicron hydrophobic agent dispersions. These examples can be utilized as presented or can be diluted in water or water miscible solvent to a concentration that is optimized for a given application. They can also be combined in various ratios to provide multiple benefits to the consumer.

Example 1

Moisturizing Hand Sanitizer

A dispersion composition of the invention was used to create a product with the following composition:

TABLE

Moisturizing Hand Sanitizer

| Raw Material | % (wt) |
| --- | --- |
| SDA 40-B 190 (EtOH) | 60.80 |
| Fragrance | 0.40 |
| Ultrez 20 (crosslinked copolymer of alkyl acrylate) | 0.50 |
| AMP Ultra PC-1000 | 0.45 |
| BHT (antioxidant) | 0.05 |
| Glycerin | 5.00 |
| Butylene Glycol | 3.00 |
| Water | 9.80 |
| Substantially surfactant-free Submicron Dispersion of Olive Oil (25%) and *Echium* Seed Oil (5%) | 10.00 |
| Substantially surfactant-free Submicron Dispersion of dimethicone (30%) | 10.00 |
| | 100.0 |

The composition enables the user to overcome the typical drawbacks of conventional hand sanitizers. In addition to performing sanitization, this composition helps to restore the balance of the skin barrier, providing moisturization and replenishing natural fatty acids that would normally be stripped during the use of a high alcohol product.

Example 2

Cooling Cologne

A dispersion composition of the invention was used to create a product with the following composition:

TABLE

Moisturizing Cologne

| Raw Material | % (wt) |
| --- | --- |
| SDA 40-B 190 | 50.00 |
| Fragrance | 3.50 |
| Ultrez 20A (acrylate/alkyl acrylate crosspolymer) | 0.50 |
| BHT | 0.05 |
| Glycerin | 5.00 |
| Bisabolol (anti-irritant) | 0.30 |
| Water | 19.15 |
| Substantially surfactant-free Submicron Olive oil (25%) and *Echium* Seed Oil (5%) Dispersion | 10.00 |
| Substantially surfactant-free Submicron dimethicone (30%) Dispersion | 10.00 |
| Spherica P-1500 (spherical silica) | 0.50 |
| Tris Amino (30% Aq) | 1.00 |
| | 100.0 |

This composition enables the application of fragrance to the skin while providing a pleasant cooling sensation without disrupting the natural skin barrier. The composition helps to restore essential lipids to the skin surface and is a unique method of delivering the fragrance.

Example 3

Lubricating (Low Irritation) Shave Gel

A dispersion composition of the invention was used to create a product with the following composition:

TABLE

Low Irritation Shave Gel

| Raw Material | % (wt) |
| --- | --- |
| Water | 43.35 |
| Ultrez-10 (Acrylate/alkyl acrylate crosspolymer) | 0.90 |
| Glycerin | 24.15 |
| Benzyl Alcohol | 0.65 |
| Substantially surfactant-free Submicron Silicone elastomer (30%) dispersion | 7.70 |
| Substantially surfactant-free Submicron dimethicone (30%) dispersion | 7.70 |
| TiO2 3328 | 1.00 |
| Pentylene Glycol | 3.80 |
| Actiphyte Chamomite GL | 1.00 |
| Actiphyte Lavender GL | 1.00 |
| Farnesol | 0.50 |
| Salicylic Acid | 0.20 |
| Urea | 2.50 |
| Triacetin | 0.50 |
| Allantoin (soothing agent) | 0.50 |
| LEMC (or other humectant blends) | 3.80 |
| Sodium Hydroxide (30% Aq) | 0.75 |
| | 100.0 |

This composition delivers a soothing shaving experience without the negatives associated with typical shaving products. The submicron dispersion composition provides skin protecting dimethicone to the sensitive shave areas, and incorporates therapeutic agents to condition the skin and minimize any irritation that would typically occur during shaving.

Example 4

Ethyl Alcohol-Free Exfoliation Mask

A dispersion composition of the invention was used to create a product with the following composition:

TABLE

Exfoliator - Ethyl Alcohol Free

| Raw Material | % (wt) |
| --- | --- |
| Water | 25.00 |
| Glycerin | 10.00 |
| Keltrol CG-RD (Xanthan gum) | 0.700 |
| Butylene Glycol | 20.00 |
| Salicylic Acid | 2.00 |
| Sepinov EMT-10 (rheological modifying agent) | 0.75 |
| Purac Hi-Pure Lactic Acid | 10.00 |
| Tartaric Acid NF/FCC Granular | 1.00 |
| Water | 13.80 |
| Substantially surfactant-free | 10.00 |

TABLE-continued

Exfoliator - Ethyl Alcohol Free

| Raw Material | % (wt) |
|---|---|
| Submicron dispersion of dimethicone (30%) | |
| Substantially surfactant-free Submicron dispersion of a Silicone elastomer (30%) | 2.50 |
| Allantoin | 0.25 |
| Sodium Hydrox. 30% Aqueous | 4.00 |
| | 100.0 |

This composition provides highly effective exfoliation with alpha and beta hydroxy acids in a form that mitigates irritation. The submicron dispersion composition incorporates skin protecting dimethicone and a therapeutic agent to minimize the irritation that is typically associated with exfoliating products containing alpha and beta hydroxy acids.

Example 5

Alcohol-Based Exfoliation Mask

A dispersion composition of the invention was used to create a product with the following composition:

TABLE

Alcohol Exfoliating Mask

| Raw Material | % (wt) |
|---|---|
| Water | 38.80 |
| Glycerin | 10.00 |
| Keltrol CG-RD | 0.70 |
| SDA 40-B 190 | 20.00 |
| Salicylic Acid | 2.00 |
| Substantially surfactant-free Submicron dispersion of dimethicone (30%) | 10.00 |
| Substantially surfactant-free Submicron dispersion of Silicone elastomer (30%) | 2.50 |
| Allantoin | 0.25 |
| Purac Hi-Pure Lactic Acid | 10.00 |
| Tartaric Acid NF/FCC Granular | 1.00 |
| Citric Acid 30% Aqueous | 0.00 |
| Sodium Hydroxide 30% Aqueous | 4.00 |
| Tris Amino 30% Aqueous | 0.00 |
| Sepinov EMT-10 | 0.75 |
| | 100.0 |

This composition provides highly effective exfoliation with alpha and beta hydroxy acids in a form that both refreshes the skin and mitigates irritation. The submicron dispersion composition incorporates skin protecting dimethicone and a therapeutic agent to minimize the irritation that is typically associated with exfoliating products containing alpha and beta hydroxy acids.

The invention can be further described with respect to the following exemplary embodiments:

A. A composition for application to skin, hair or external mucosa comprising one of: (A) a skin, hair or mucosal composition comprising (1): a) a substantially surfactant-free dispersion of submicron particles of hydrophobic agent(s) in an aqueous-solvent fluid, wherein the substantially surfactant-free dispersion of submicron particles of hydrophobic agent(s) has an average particle size from 100 nm to 999 nm, and wherein the hydrophobic agent(s) comprise about 0.01% wt. to about 70% wt. of the dispersion composition; and b) rheological modifying agent(s); wherein the aqueous-solvent fluid, including the aqueous-solvent fluid of the dispersion, is 10% to 95% wt. of one or more water miscible solvent(s), and 4.99% to 89.99% wt. water, and 0.01% to 10% wt. of the rheological modifying agent(s); or (B) the skin, hair or mucosal composition comprising (2): 1) dispersed submicron particles of hydrophobic agent(s) having average particle size from 100 nm to 999 nm; 2) an aqueous-solvent fluid; and 3) rheological modifying agent(s); wherein the aqueous-solvent fluid is 10% to 95% wt. of one or more water miscible solvent(s), 4.99% to 89.99% wt. water, and 0.01% to 10% wt. of the rheological modifying agent(s); and wherein the hydrophobic agents comprise 0.01 to 70% wt. of the skin, hair or mucosal composition; and wherein the composition is substantially surfactant-free; or (C) the skin, hair or mucosal composition containing a water miscible solvent comprising (3): a) a substantially surfactant-free dispersion of submicron particles of hydrophobic agent(s) in aqueous or aqueous-solvent fluid, wherein the aqueous solvent fluid of a) can be present at 0%-70% wt. and wherein the substantially surfactant-free dispersion of submicron particles of hydrophobic agent(s) has an average particle size from 100 nm to 999 nm, and wherein the hydrophobic agent(s) comprise about 0.01% wt. to about 70% wt. of the dispersion composition; b) water, an aqueous-solvent fluid or a water miscible solvent; wherein the water miscible solvent can be present at 0%-95% wt. and c) rheological modifying agent(s); wherein the final composition contains an aqueous-solvent fluid, including the aqueous or aqueous-solvent fluid of the dispersion, is 10% to 95% wt. of one or more water miscible solvent(s), and 4.99% to 89.99% wt. water, and 0.01% to 10% wt. of the rheological modifying agent(s).

B. The dispersion composition of Embodiment A, wherein 80% weight or more of the water miscible solvent is a mono-, di- or poly-hydroxy compound of the formula

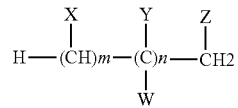

where X, Y and Z are independently —H or —OH; W is independently —H or —CH3; m is 0 or 1; and n is an integer from 0 to 6.

C. The composition of Embodiment A or B, formulated as a moisturizing hand sanitizer comprising a water miscible solvent that is 50% to 89.99% by volume, or in another embodiment by wt, ethanol or isopropanol.

C'. The composition of Embodiment A or B, formulated as a moisturizing hand sanitizer comprising a water miscible solvent that is 50% to 89.99% by volume ethanol or isopropanol.

D. The composition of Embodiment A, B or C, formulated as a cooling cologne.

E. The cologne of Embodiment D, comprising a water miscible solvent that is 20% to 70% by volume, or in another embodiment by weight, ethanol.

F. The composition of Embodiment A, and B, formulated as a body lotion.

F'. The composition of Embodiment F, wherein the body lotion comprises 10% to 80% wt. of one or more water miscible solvent(s) that is a mono-, di-, or poly-hydroxy compound of the formula:

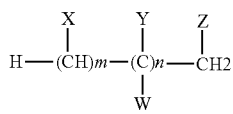

wherein X, Y and Z are independently —H or —OH; W is independently —H or —CH3; m is 0 or 1; and n is an integer from 0 to 6.

G. The body lotion of Embodiment F, comprising 10% to 50% wt. of a water miscible solvent of Embodiment B.

H. The composition of Embodiment A and B, formulated as an exfoliating mask.

H'. The composition of Embodiment H, comprising 10% to 80% wt. of one or more water miscible solvent(s) that is a mono-, di-, or poly-hydroxy compound of the formula:

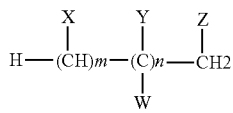

wherein X, Y and Z are independently —H or —OH; W is independently —H or —CH3; m is 0 or 1; and n is an integer from 0 to 6.

I. The mask of Embodiment H, comprising, 10% to 40% wt. of a water miscible solvent of Embodiment B.

J. The composition of Embodiment A and B, formulated as a lubricating shaving gel or cream.

K. The composition of Embodiment A-J, wherein the composition further comprises therapeutic agents, which can be hydrophobic agents.

L. The composition of Embodiment A-J, wherein the composition further comprises one or more aesthetic modifying agent(s), wherein the aesthetic modifying agent(s) can be hydrophobic agent(s).

L'. The composition of Embodiment A-J, wherein the composition further comprises one or more therapeutic agent(s) and aesthetic modifying agent(s), both of which can be hydrophobic agent(s).

M. A method of applying a therapeutic agent to skin, hair or external mucosa of a human or animal comprising applying to such tissue a composition of Embodiment A-L', that further comprises an effective amount of the therapeutic agent.

M'. A method of applying one or more therapeutic agent(s) to skin, hair or external mucosa comprising applying to the skin, hair, or external mucosa of a human or animal the composition of Embodiment A-L', wherein the composition further comprises an effective amount of the one or more therapeutic agent(s), and wherein the one or more therapeutic agents further comprises one or more hydrophobic agents.

N. A method of imparting a desirable tactile, olfactory, or visual property to a skin, hair or mucosal surface of a human or animal comprising applying to such tissue a composition of Embodiment A-L', that further comprises an effective amount of one or more aesthetic modifying agents.

N'. A method of imparting a desirable tactile, olfactory, or visual property to a skin, hair, or mucosal surface of a human or animal comprising applying to the skin, hair, or mucosal surface a composition of Embodiment A-L', wherein the composition further comprises an effective amount of one or more aesthetic modifying agents, and wherein the one or more aesthetic modifying agents further comprises one or more hydrophobic agent.

O. A composition or method of one of the foregoing embodiments, wherein the composition is 0.01% to 85% by wt. of the substantially surfactant-free dispersion of submicron particles of hydrophobic agent(s).

While the foregoing is directed to embodiments of the present disclosure, other and further embodiments of the disclosure may be devised without departing from the basic scope thereof.

The invention claimed is:

1. A composition for application to skin, hair or external mucosa comprising:
    an aqueous-solvent fluid and submicron particles of hydrophobic agent(s) of average particle size from 100 nm to 999 nm dispersed and suspended in the aqueous-solvent fluid, wherein the submicron particles are 90% wt. or more non-polar, wherein 85% or more of the submicron particles have a size within 300 nm of the average particle size;
    wherein the aqueous-solvent fluid comprises
        30% to 95% wt. of one or more water miscible solvent(s),
        4.99% to 70% wt. water, and
        0.01% to 10% wt. of one or more rheological modifying agent(s);
    wherein 70% wt. or more of the one or more water miscible solvents, and 30% wt. or more of the aqueous-solvent fluid, is one or more mono- or di-hydroxy compounds selected from the group consisting of $C_2$ or $C_3$ alcohols, propylene glycol, butylene glycol or pentylene glycol;
    wherein the hydrophobic agent(s) comprise 0.01 to 70% wt. of the skin, hair or mucosal composition; wherein the composition is substantially surfactant-free, wherein the amount of surfactant, if present, is not sufficient to materially lower the surface tension of the aqueous-solvent fluid; and wherein the dispersed submicron particles are stable.

2. The composition of claim 1, wherein 80% weight or more of the water miscible solvent is one or more of said mono- or di-hydroxy compounds.

3. The composition of claim 1, wherein the composition is formulated as a moisturizing hand sanitizer, and wherein the composition comprises about 50% to 90% by weight ethanol or isopropanol.

4. The composition of claim 1, wherein the composition is formulated as a cooling cologne, and wherein the composition comprises about 50% to 90% by weight ethanol.

5. The composition of claim 1, wherein the composition is formulated as a body lotion, and wherein the composition comprises 30% to 80% wt. of said one or more water miscible solvent(s).

6. The composition of claim 1, wherein the composition is formulated as an exfoliating mask, and wherein the composition comprises 30% to 80% wt. of one or more of said one or more water miscible solvent(s).

7. The composition of claim 1, formulated as a lubricating shaving gel or cream.

8. The composition of claim 1, wherein the hydrophobic agent(s) comprises one or more therapeutic agent(s).

9. The composition of claim 1, wherein the hydrophobic agent(s) comprises at least one aesthetic modifying agent.

10. The composition of claim 1, wherein the hydrophobic agent(s) comprise one or more therapeutic agent(s) and at least one aesthetic modifying agent(s).

11. The composition of claim 1, further comprising one or more of a therapeutic agent(s), selected from the group consisting of anti-acne agents, antimicrobial agents, anti-inflammatory agents, analgesics, anti-erythemal agents, anti-pruritic agents, anti-edemal agents, anti-psoriatic agents, antifungal agents, skin protectants, sunscreen agents, vitamins, antioxidants, scavengers, anti-irritants, anti-bacterial agents, antiviral agents, antiaging agents, photoprotection agents, hair growth enhancers, hair growth inhibitors, hair removal agents, antidandruff agents, anti-seborrheic agents, exfoliating agents, wound healing agents, anti-ectoparasitic agents, sebum modulators, immunomodulators, hormones, botanicals, moisturizers, astringents, sensates, antibiotics, anesthetics, steroids, tissue healing substances, tissue regenerating substances, amino acids, peptides, minerals, ceramides, biohyaluronic acids, and bleaching ingredients.

12. The composition of claim 1, further comprising at least one therapeutic agent, which comprises at least one sunscreen agent selected from the group consisting of ethylhexyl methoxycinnamate, avobenzone, benzophenones, octocrylene, ethylhexyl salicylate, homomenthyl salicylate, triethanolamine salicylate, menthyl anthranilate, PABA, octyl dimethyl PABA, 2-ethoxyethyl p-methoxycinnamate, phenylbenzimidazole sulfonic acid, titanium dioxide and zinc oxide.

13. The composition of claim 9, wherein said the one or more aesthetic modifying agent comprises at least one compound selected from the group consisting of
   (a) a compound having the formula $C_pH_{(2p+2q)}$ wherein p is a positive integer greater than or equal to 6 and q is 0 or a positive, even integer no greater than p;
   (b) a compound having the formula B or C

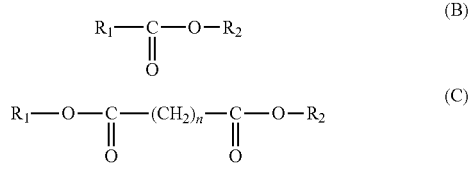

wherein $R_1$ is a saturated or unsaturated, linear, branched or cyclic $C_1$-$C_{23}$ alkyl group; and $R_2$ is hydrogen or a saturated or unsaturated, linear, branched or cyclic $C_1$-$C_{24}$ alkyl group, and n is an integer from 0 to 20; and
   (c) a silicone.

14. The composition of claim 9, wherein said aesthetic modifying agent comprises at least one compound selected from the group consisting of polysiloxanes, cyclic siloxanes, polyalkylsiloxanes, polyarylsiloxanes, polyalkylarylsiloxanes, polysiloxane gums and polyethersiloxane copolymers.

15. The composition of claim 1, wherein 90% or more of the one or more water miscible solvent(s) is (i) is one or more of said mono- or di-hydroxy compounds.

16. The composition of claim 1, wherein the submicron particles have an average particle size in the range between about 100 nm to about 500 nm.

17. The composition of claim 1, wherein the submicron particles have an average particle size in the range between about 150 nm to about 500 nm.

18. The composition of claim 9, wherein the one or more aesthetic modifying agents comprises one or more of C2-C26 alkyl substituted with 2-24 hydroxyls, wherein the hydroxyls of the foregoing compounds are independently acylated with a saturated, unsaturated, linear, branched or cyclic C1-C24 alkane, rendering the substituted alkyls hydrophobic agents.

19. The composition of claim 1, wherein said one or more mono- or di-hydroxy compounds are selected from the group consisting of ethanol, isopropanol, propylene glycol, butylene glycol, and pentylene glycol.

20. A method of applying one or more therapeutic agent(s) to skin, hair or external mucosa comprising applying to the skin, hair, or external mucosa of a human or animal the composition of claim 8.

21. A method of imparting a desirable tactile, olfactory, or visual property to a skin, hair, or mucosal surface of a human or animal comprising applying to the skin, hair, or mucosal surface a composition of claim 9.

* * * * *